US007452727B2

(12) United States Patent
Hennig et al.

(10) Patent No.: US 7,452,727 B2
(45) Date of Patent: Nov. 18, 2008

(54) METHOD FOR INCREASING CLINICAL SPECIFICITY WHEN DETECTING TUMORS AND THEIR PRECURSOR STAGES BY SIMULTANEOUSLY MEASURING AT LEAST TWO DIFFERENT MOLECULAR MARKERS

(75) Inventors: Guido Hennig, Cologne (DE); Ralph Wirtz, Cologne (DE); Kerstin Bohmann, Krefeld (DE); Birge Schopper, Pulheim (DE)

(73) Assignee: Siemens Healthcare Diagnostics Inc, Tarrytown, NY (US)

( * ) Notice: Subject to any disclaimer, the term of this patent is extended or adjusted under 35 U.S.C. 154(b) by 54 days.

(21) Appl. No.: 10/023,501

(22) Filed: Dec. 17, 2001

(65) Prior Publication Data

US 2002/0123845 A1 Sep. 5, 2002

(30) Foreign Application Priority Data

Dec. 18, 2000 (DE) ............................... 100 63 112

(51) Int. Cl.
*G01N 33/48* (2006.01)
*G01N 33/50* (2006.01)
*G01N 33/53* (2006.01)
*G01N 1/30* (2006.01)
*C12Q 1/00* (2006.01)

(52) U.S. Cl. ............................ 436/64; 436/56; 436/63; 436/164; 436/172; 436/813; 435/4; 435/7.1; 435/7.21; 435/7.23; 435/40.5; 702/19

(58) Field of Classification Search .................. 436/64, 436/56, 63, 164, 171, 172, 811, 813; 435/7.21, 435/7.23, 40.5, 4, 7.1; 702/19
See application file for complete search history.

(56) References Cited

U.S. PATENT DOCUMENTS

| 5,109,429 | A | * | 4/1992 | Bacus et al. | ................. | 436/183 |
| 5,544,650 | A | | 8/1996 | Boon et al. | ................. | 128/632 |
| 5,733,721 | A | | 3/1998 | Hemstreet et al. | .............. | 435/6 |
| 5,741,648 | A | | 4/1998 | Hemstreet et al. | .............. | 435/6 |
| 5,932,412 | A | | 8/1999 | Dillner et al. | | |
| 6,005,256 | A | | 12/1999 | McGlynn et al. | ......... | 250/559.4 |
| 6,007,996 | A | | 12/1999 | McNamara et al. | | |
| 6,077,996 | A | * | 6/2000 | Klenke | .................... | 800/320.1 |
| 6,248,063 | B1 | * | 6/2001 | Barnhill et al. | ............. | 600/300 |
| 2002/0123845 | A1 | | 9/2002 | Henning et al. | | |

FOREIGN PATENT DOCUMENTS

WO 9921014 4/1999
WO 0024760 5/2000

OTHER PUBLICATIONS

Williams, G., Romanowski, P., Morris, L., Madine, M., Mills, A., Stoeber, K., Marr, J., Laskey, R., Coleman, N., "Improved Cervical Smear Assessment Using Antibiotics Against Proteins That Regulate DNA Replication", Proc. Natl. Acad. Sci. USA, 95: 14932-14937 (Dec. 1998).
Cuzick, J., "Human Papillomavirus Testing For Primary Cervical Cancer Screening", JAMA, 283: 108-109 (Jan. 2000).
Tervahauta, A., Syrjanen, S., Mantyjarvi, R., Syrjanen, K., "Detection of p53 Protein and Ki-67 Proliferation Antigen in Human Papillomavirus (HPV)-Positive and HPV-Negative Cervical Lesions by Immunohistochemical Double-staining", Cytopathology, 5: 282-293 (1994).
Boon, M., Beck, S., Kok, L., "Semiautomatic PAPNET Analysis of Proliferating (MiB-1-Positive) Cells in Cervical Cytology and Histology", Diag. Cytopathology, 13: 423-428 (1995).
Sawaya, G., Washington, A., "Cervical Cancer Screening: Which Techniques Should Be Used and Why?", Clin. Obstetrics and Gynecology, 42: 922-938 (1999).
Sano, T., Oyama, T., Kashiwabara, K., Fukuda, T., Nakajima, T., "Immunohistochemical Overexpression of p16 Protein Associated with Intact Retinoblastoma Protein Expression in Cervical Cancer and Cervical Intraepithelial Neoplasia", Path. Int., 48: 580-585 (1998).
Gomez, F., Roldan, M., Corcuera, M., Picazo, A., Munoz, E., Alonso, M., "Simultaneous Detection of Antigens and Specific DNA Sequences of Human Papillomavirus in Uterine Cervical Biopsy Specimens. Description of a Double-Labelling Technique1", Eur. J. Histochem., 41: 255-259 (1997).
Stoler, M., "Advances in Cervical Screening Technology", Mod. Pathol., 13: 275-284 (2000).
Leek, R., Kaklamanis, L., Pezzella, F., Gatter, K., Harris, A., "bcl-2 in Normal Human Breast and Carcinoma, Association With Oestrogen Receptor-Positive, Epidermal Growth Factor Receptor-Negative Tumours and In Situ Cancer", Br. J. Cancer, 69: 135-139 (1994).
Oshika, Y., Nakamura, M., Tokunaga, T., Fukushima. Y., Abe, Y., Ozeki, Y., Yamazaki, H., Tamaoki, N., Ueyama, Y., "Multidrug Resistance-Associated Protein and Mutant p53 Protein Expression in Non-Small Cell Lung Cancer", Mod. Pathol., 11: 1059-1063 (1998).
Kraeft, S., Sutherland, R., Gravelin, L., Hu, G., Ferland, L., Richardson, P., Elias, A., Chen, L., "Detection and Analysis of Cancer Cells in Blood and Bone Marrow Using a Rare Event Imaging System", Clin. Cancer Research, 6: 434-442 (Feb. 2000).
Reiner, A., Neumeister, B., Spona, J., Reiner, G., Schemper, M., Jakesz, R., "Immunoyctochemical Localization of Estrogen and Progesterone Receptor and Prognosis in Human Primary Breast Cancer", Cancer Research, 50: 7057-7061 (Nov. 1990).
Mokbel, K., Parris, C., Ghilchik, M., Williams, G., Newbold, R., "The Association Between Telomerase, Histopathological Parameters, and KI-67 Expression in Breast Cancer", Am. J. Surgery, 178: 69-72 (1999).
Rao, J., Apple, S., Hemtreet, G., Jin, Y., Nieberg, R., "Single Cell Multiple Biomarker Analysis in Archival Breast Fine-Needle Aspiration Specimens: Quantitative Fluorescence Image Analysis of DNA Content, p53, and G-actin as Breast Cancer Biomarkers", Cancer Epidemiology, Biomarkers & Prevention, 7: 1027-1033 (1998).

(Continued)

*Primary Examiner*—Maureen M Wallenhorst
(74) *Attorney, Agent, or Firm*—Siemens Corporation

(57) ABSTRACT

The present invention relates to an automatable method for the improved diagnosis of pathologically altered cells by simultaneously staining at least two different molecular markers, which exhibit a change in gene expression which is disease-associated, in a cell or constituent regions of a tissue sample by means of using combinations of antibodies and accrediting signal intensities.

8 Claims, No Drawings

OTHER PUBLICATIONS

Valdiguie, P., "Role and Use of Expert Systems Within the Clinical Laboratory", Clinica Chimica Acta, 278: 193-202 (1998).

Neel, T., Moreau, A., Laboisse, C., Truchaud, A., "Comparative Evaluation of Automated Systems in Immunohistochemistry", Clinica Chimica Acta, 278: 185-192 (1998).

Hopman, A., "Rapid Synthesis of Biotin-, Digoxigenin-, Trinitrophenyl-, and Fluorochrome-Labeled Tyramides and Their Application for In Situ Hybridization Using CARD Amplification", J. of Histochem. & Cytochem., 46: 771-777 (1998).

Bergeron, C., "Human Papillomaviruses Associated with Cervical Intraepithelial Neoplasia", Am. J. Surgical Pathology, 16(7): 641-649, 1992.

Busmanis, I., "Biomarkers in Carcinoma of the Cervix, Emphasis on Tissue-related Factors and their Potential Prognostic Factors", Ann. Acad. Med. Singapore, 27: 641-645, 1998.

Skomedal, H., "Aberrant Expression of the Cell Cycle Associated Proteins TP53, MDM2, p21, p27, cdk4, Cyclin D1, RB and EGFR in Cervical Carcinomas", Gynecologic Oncology 73: 223-228, 1999.

Mitra, "ERBB2 (HER2/neu) Oncogene is Frequently Amplified in Squamous Cell Carcinoma of the Uterine Cervix", Cancer Research 54: 637-639, 1994.

Radhakrishna Pillai, M., "The Presence of Human Papillomavirus-16/-18 E6, p53, and Bcl-2 protein in Cervicovaginal Smears from Patients with Invasive Cervical Cancer", Cancer Epidemiology, Biomarkers & Prevention, 5: 239-335, May 1996.

Kersemaekers, A.-M., "Oncogene Alterations in Carcinomas of thew Uterine Cervix: Overexpression of the Epidermal Growth Factor Receptor is Associated with Poor Prognosis", Clinical Cancer Research, 5: 577-586, Mar. 1999.

Munirajan, A.K., "The Status of Human Papillomavirus and Tumor Suppressor Genes p53 and p16 in Carcinomas of Uterine Cervix from India", Gynecologic Oncology 69: 205-209, 1998.

* cited by examiner

METHOD FOR INCREASING CLINICAL SPECIFICITY WHEN DETECTING TUMORS AND THEIR PRECURSOR STAGES BY SIMULTANEOUSLY MEASURING AT LEAST TWO DIFFERENT MOLECULAR MARKERS

STATE OF THE ART

Cancer diseases still constitute one of the most frequent causes of death world-wide. There is a clinical need for both the early recognition and specific detection of cancer and precancerous stages. Moreover, further, more detailed characterization of the tumour is important in order to draw conclusions with regard to therapy and prognosis. This is useful since different carcinoma subtypes react differently to the therapeutic measures which are applied. For this, for example when breast cancer is suspected, recourse is ever more frequently taken to immunohistochemical staining of molecular markers, for example cytokeratins, oestrogen receptor, her2/neu, Ki67 or p53 (e.g. Leek et al., 1994, Br. J. Cancer, 69, 135-139; Mokbel et al., 1999, Am. J. Surgery, 178, 69-72; Reiner et al., 1990, Cancer Res., 50, 7057-7061). While this staining is most frequently performed on breast biopsies, it is also increasingly carried out on needle punctures (FNAs=fine needle aspirates). Molecular markers are also employed in connection with deciding whether the tumour is a primary tumour or a metastasis. The expression of markers which are, for example, specific for the primary organ affected facilitates this identification.

In recent years, a large number of genes have been identified which express their proteins in an altered manner as a result of mutations and consequently play a role in the genesis of cancer. The corresponding proteins are detected, as diagnostic markers, both in serum and at the cellular level. These proteins are involved in a multiplicity of physiological regulator processes in the cell, such as growth control (proliferation genes, e.g. Ki67 and mcm-5; oncogenes and tumour suppressor genes, e.g. p16, EGF receptor, her2/neu and mdm-2), apoptosis (natural cell death, e.g. p53 and bcl-2), DNA repair (msh-1) and cell adhesion (E-cadherin, β-catenin and APC). Immunohistochemical and immunocytochemical detection methods using specific antibodies against these proteins (van Noorden, 1986, Immunocytochemistry, Modern Methods and Applications, 2nd edition, Wright, Bristol, 26-53) are, for example, suitable for the detection.

It has been demonstrated many times that a single marker does not achieve sufficient specificity with regard to recognizing pathologically altered cells since it is also present in some healthy cells. This is due to the fact that these markers can be proteins which are involved in physiological regulatory processes in healthy cells and it is only an excessively high expression which is an indication of a pathologically altered cell. Williams et al. (1998, PNAS, 95, 14932-14937) describe the DNA replication marker mcm-5, which detects 28 tested lesions/tumours in cervical smears (n=58) but stains 2 out of 28 normal smears in a falsely positive manner. Sano et al. (Pathology Intl., 1998, 48, 580-585) report that the marker p16 nonspecifically stains 3 out of 15 normal cervical biopsies. While HPV can be detected in virtually 100% of all lesions and tumours of the cervix, it can also be detected in many normal cervical epithelia; i.e. while a test for detecting HPV exhibits a high degree of sensitivity, it only exhibits a low degree of specificity (e.g. Cuzick, 2000, JAMA, 283, 108-109).

In pathology, it is increasingly of interest to detect several markers in a biological sample. On the one hand, more information is then available for detecting and characterizing pathologically altered cells or tissue regions; on the other hand, it is then possible to recognize the nonspecific staining of individual markers for what it is and consequently avoid incorrect conclusions. Traditionally, serial sections of an available biopsy or several preparations of a body sample (e.g. uterine cervical smear in fixative) are prepared for this purpose and in each case stained with a specific marker. This method has several disadvantages: high consumption of the patient sample material, which is usually limited, and of staining reagents, the large amount of time required and the high costs, and also no possibility of unambiguously colocating two or more markers in a cell or particular areas of the tissue sample. While the simultaneous detection of two or more different biological markers in a biological sample has already been described in the literature (DAKO, Practical Guide for Immunoenzymatic Double Staining Methods; Gomez et al., Eur. J. Histochem., 1997, 41, 255-259), it has not so far been used in routine diagnosis since the protocols have not been standardized to any extent. Terhavauta et al. (Cytopathology, 1994, 5, 282-293) make use of a double staining of p53 and Ki67 in biopsies taken from cervical lesions and are able to detect both markers in basal and parabasal cells from HPV-positive and HPV-negative lesions, in some cases in one cell. At the same time, however, the authors do not use the information, by combining the results, to draw a secure conclusion with regard to the presence of tumour cells in this sample. There is a complete lack of any attempt to use the staining information with a view to automating the detection of tumour regions. Furthermore, apart from this one combination, there is no mention of any other marker combinations which might be able to facilitate the identification and characterization of the tumour region.

Further double stainings performed on tumour biopsies of the lung are mentioned in Kraeft et al. (Clin Cancer Res. 2000, 6, 434-442) and Oshika et al (Mod Pathol, 1998, 11, 1059-1063). The antibody combinations which are described in these references are completely different from the combinations on which the present invention is based. Furthermore, both the abovementioned publications additionally require a pathologist, who assesses the staining of the biopsies, for making the diagnosis. This approach is conceptually incompatible with automating the method and has therefore so far never been taken into consideration.

Rao et al. (1998, Cancer Epidemiology, Biomarkers and Evolution, 7, 1027-1033) describe the multiple staining of a variety of tumour-associated markers (DNA content, G-actin and p53) in needle puncture material (FNA, fine needle aspirates) taken from the breast. They interpret their results to the effect that the use of several markers achieves a higher clinical specificity than that achieved when observing the individual markers and can consequently play an important role in the early recognition of breast cancer. The multiple staining cited by the authors is restricted to needle puncture material obtained from the breast and, because of the different material properties, cannot be applied to other biological materials (i.e. biopsies and cervical smears). Furthermore, the marker combinations differ from the combinations which are mentioned in the present invention. There is no attempt to use the staining information with a view to automating the detection of tumour regions.

A further improvement in present clinical tumour diagnosis consists both in the automation of sample preparation and staining and in automated image analysis including establishment of the diagnosis. In addition to saving time and requiring fewer staff, this approach also results in a more objective, and consequently more uniform, diagnosis. Staining of biological markers in tumour cells or their precursors with fluorescence or using chromogenic dyes makes it possible to quantify the signals and consequently read them in an automated manner. Systems which enable staining protocols to be performed in an automated manner already exist. However, image analysis is not used to achieve an automated diagnosis (LeNeel et al, Clin Chim Acta, 1998, 278, 185-192). The most advanced system is that involving the automated detection of tumour cells and their precursors in cervical smears using morphological image information (Sawaya et al., Clinical Obstetrics and Gynecology, 1999, 42, 922-938; Stoler, 2000, Mod. Pathol., 13, 275-284). In addition to the automated morphological detection of abnormal cells in cervical smears using the PAPNET system, Boon et al. (1995, Diagn. Cytopathol., 13, 423-428) additionally make use of the immunohistochemical staining of proliferating cells employing Ki67 antibodies. However, the use of this one molecular marker does not enable any clear distinction to be made between benign proliferating cells and carcinogenic cells. However, these authors in no way deal with using the simultaneous detection of at least two molecular markers for identifying abnormal cells.

The patent of which Boon et al. are authors (U.S. Pat. No. 5,544,650) describes how staining with an immunohistochemical marker facilitates the automated detection of proliferating (carcinogenic and non-carcinogenic) cells in a sample and how, in a semiautomated process, the controlling pathologist/cytologist decides whether the stained cells truly are carcinogenic cells. However, there is no mention of any specific antibody combinations which would enable abnormal or tumour cells to be detected in an automated manner.

The U.S. Pat. No. 6,005,256, whose authors are McGlynn and Akkapeddi, provides a detailed description of an appliance and a method for simultaneously detecting several fluorescence-labelled markers in a body sample, including for the purpose of identifying cancer cells, without, however, dealing with any specific application in cancer diagnosis or mentioning appropriate marker combinations possessing increased specificity.

It is known that Ampersand Medical Systems Group (www.ampersandmedical.com) is developing a new system for screening cervical smears (InPath) which, in addition to the Company's own in-house sample preparation, also involves the use of fluorescence to detect unspecified biological markers.

OBJECT

The present invention describes an automatable method which can be employed for determining pathologically altered cells, preferably cancer cells and their precursors, by means of using defined marker combinations.

According to the invention, this is achieved by means of the subject-matter which is detailed in the patent claims.

SUMMARY OF THE DESCRIPTION/ACHIEVEMENT OF THE OBJECT

The present invention is based on the applicants' findings that the specificity of the detection of pathologically altered cells, preferably carcinomas and their precursors, is increased by simultaneously detecting at least two specific molecular markers, namely disease-associated changes in gene expression, in a cell or tissue sample, and that a more specific detection, and one that, in addition, can also be automated, is made possible on the basis of detecting several markers and of combining and accrediting the signals.

DETAILED DESCRIPTION

The invention relates to molecular markers which, when detected individually, do not achieve sufficient specificity with regard to recognizing pathologically altered cells or tissues since they are also present, in similar or different quantity, in some biological material which is not pathologically altered. This is based on the fact that these markers can be proteins which are involved in physiological regulatory processes in healthy cells as well. In addition to this, the detection of the molecular marker may not be unambiguous because of the antibody crossreacting in a nonspecific manner, with this being manifested in the staining of particles of the biological material which do not contain the molecular marker. The inventors have observed that, by simultaneously detecting at least two markers in a cell, or within a constituent region of the biological material, e.g. within a narrowly defined region of a tissue section, it is possible to compensate for the deficient specificity of the single marker detection so as to ensure a higher degree of specificity when detecting abnormal cells or tissue segments. Combining several markers when diagnosing biological samples thus makes the informative value higher then it is when using single markers.

The marker combinations comprise the visualization of the altered expressions of genes belonging to at least one of the following classes: oncogenes, tumour suppressor genes, apoptosis genes, proliferation genes, repair genes and viral genes, as shown, by way of example, by combinations of the molecular markers her2/neu, p16, p53, Ki67, MN, mdm-2, bcl-2 and EGF receptor. The following combinations are preferably intended: her2/neu and Ki67, her2/neu and p53, her2/neu and bcl-2, her2/neu and p16, bcl-2 and Ki67, bcl-2 and p53, bcl-2 and p16, p16 and p53, p16 and Ki67.

According to the invention, the applicants' findings are used for a method for the early diagnosis of disease-associated cells or tissue segments, which method comprises the detection of combinations of the above-described molecular markers with the aim of detecting carcinomas and their precursors, and also, where appropriate, the origin of metastases, in an automated manner. The automated and specific detection of tumour cells can be achieved by the following method: in the first place, these two signals must be present in a cell or a restricted area of the body sample and, in the second place, the signals given by the two markers must in each case be above or below an individually defined intensity or threshold value. When these two criteria are applied, it is possible to rule out healthy cells which are, for example, expressing a marker above the set threshold or which exhibit both markers below the signal strength which is defined in each case.

The expression "molecular marker" encompasses molecular changes in cells, in particular changes in gene expression, which have been observed in connection with a cell constitution which is changed or which is pathological. Methods for detecting molecular markers comprise any methods which determine the quantity or quality of the markers, preferably at the protein level.

The use of antibodies or other specific binding proteins (e.g. anti-cullins), which permit subsequent cytochemical or histochemical detection involving chromogenic and/or fluorescent detection, is suitable for detection at the protein level.

The expression "simultaneous detection of at least two specific molecular markers" encompasses methods which visualize at least two gene expressions in a body sample, in particular in a single preparation of the body sample as well, such that the gene expressions can be viewed in conjunction with each other. In this connection, it is not only the presence of at least two signals, but also the presence or absence of one or more additional signals, which is of possible combinatorial informative value. In addition to the tumour specificity, this further information could comprise a conclusion with regard to the origin of a metastasis. In this connection, it is of importance that the detected markers are detected in relative spatial proximity, in particular in one cell or within a narrowly defined region of the sample, for example within an area of a tissue section.

The expression "combining and accrediting the signals" encompasses the linking of at least two items of information which have been obtained on the basis of detecting at least two markers in a body sample. In addition, healthy cells can be distinguished specifically from diseased cells by defining threshold values for the marker intensities.

The expression "cell or tissue sample" encompasses cells which are isolated from body samples, such as smears, sputum, organ punctates, biopsies, secretions, cerebrospinal fluid, bile, blood, lymph fluid, urine and faeces, or tissue which has been removed from organs, such as breast, lung, intestine, skin, cervix, prostate and stomach. In this connection, a tissue sample comprises a region of functionally related cells or adjacent cells.

The expression "pathologically altered cells" encompasses carcinomas and their precursors, preferably carcinomas of the respiratory, reproductive and gastrointestinal tracts, and also tumours of the skin, of the breast and of the vascular system, in particular, however, mammary carcinoma and cervical carcinoma and its precursors, e.g. cervical intraepithelial neoplasias (CIN I-III) and also carcinoma in situ.

The expression "automatable detection" encompasses methods which replace the manual labour of human personnel either entirely or else only in constituent steps and are used, in particular, in steps of the detection method or in the subsequent documentation or information processing. This involves steps of sample preparation, sample staining, sample analysis and information processing. In this connection, the detection can be effected by means of absorption, reflection or fluorescence measurements. The method of fluorescence measurement encompasses all the methods such as fluorescence microscopy or FACS (flowthrough cytometer) analysis.

The expression "diagnostic expert system" encompasses computer software which converts the image information into a proposed diagnosis. On the basis of parameters which are present in the software, or of external information which the software can access, this expert system is able to consolidate the entire information which is available, or parts thereof, into a proposed diagnosis. If further parameters should be required for substantiating the proposed diagnosis, the software can suggest that these parameters be collected or, by coupling to suitable analytical equipment within the sense of a reflex algorithm, automatically request this.

The expression "amplification system" encompasses biochemical methods which increase the signal intensities such that a more favourable signal/noise ratio is produced for specifically detecting a molecular marker. This is normally achieved by employing additional antibodies and/or enzymic detection reactions.

The present invention can be used to specifically detect pathologically altered cells, e.g. carcinomas and their precursors, and to determine the origin of metastases. The invention also relates to a kit for implementing a method according to the invention, which kit contains the following constituents:
(a) Reagents for detecting at least two of the molecular markers, namely labelled and/or unlabelled antibodies against her2/neu, p16, p53, Ki67, MN, mdm2, bcl2 and EGF receptor.
(b) Customary auxiliary agents such as buffers, supports, signal amplification substances, staining reagents, etc.
(c) Automatable methods for preparing and staining samples and detecting signals.
(d) Protocols and reagents for staining cell lines as a control reaction.

The comments made above apply to the individual components of the kit. Individual, or several, components of the kit can also be used in altered form.

The present invention can be used to detect pathologically altered cells, e.g. carcinomas and their precursors, manually or else in methods which are partially or completely automated. Since the results, which are achieved in accordance with the invention and which are obtained from simultaneously detecting at least two molecular markers do not undergo any subjective assessment but, on the contrary, are conducive to an objective, automated detection of pathological changes in biological materials, the morphological findings can be supplemented by objective parameters, also in the form of "reflex testing". Because the methods can be operated rapidly and in an automated manner, they are suitable for large-scale screening methods which are economical with regard to costs and personnel. In addition to this, the combinatorial staining of more than two markers makes it possible to diagnose pathological changes differentially and to determine the origin of metastases.

Consequently, the present invention constitutes an important contribution to the modem diagnosis of diseases.

EXAMPLES

Protocols for carrying out the above-described invention are given below by way of example. These examples specify precise conditions which, in the present case, are preset as a result of using the Ventana automatic stainer NEXES. This in no way alters the fact that different parameters, such as incubation and washing temperatures, incubation and washing times and the concentrations of antibodies and other reagents, can be varied, i.e. can be matched to other equipment. Amplification systems which are described here can likewise be omitted, or new ones can be added, depending on the respective antibodies or DNA probes.

Description of an Experiment for Simultaneously Detecting Two Molecular Markers in Biopsies using Specific Antibodies and Employing the Nexes Automatic Immunostainer Supplied by Ventana 4-5 μm-thick paraffin sections (RM2155 microtome supplied by Leica) are firstly prepared from the biopsy tissue, which is fixed and embedded in paraffin, and the sections are dried overnight at 37° C. In order to avoid the sections floating off in association with the subsequent staining, use is made of microscope slides which are coated with silane. For the staining, the paraffin sections are deparaffinized in xylol for 2×15 min and subsequently passed through a series of decreasing alcohol concentrations (100%, 90%, 70%, 2×5 min in each case) in order to wash the xylol out once again.

The fixing with formalin results in the formation of aldehyde crosslinkages which mask antigens and consequently make them unavailable for the antibodies. As a result, a further pretreatment is necessary. The antigens are demasked for 30 min in 10 mM citrate buffer, pH 6, at 600 W in a microwave.

After the microwave pretreatment, there then follows the immunohistochemical staining in the Nexes (Ventana Medical Systems) automatic immunostainer. All the reagents, apart from the primary antibodies and the sera, are obtained, individually or in the form of kits, from Ventana Medical Systems. All the incubations take place at 37° C. The automatic stainer washes automatically after each incubation with the reagents which are described below.

First of all, the endogenous peroxidase is inactivated for 4 min with the "inhibitor" which is included in the kit. Any possible nonspecific binding sites are then blocked off for 10 min with 1.5% goat serum (from Vector). The sections are then incubated, for 30 min, with the first monoclonal antibody (her2/neu (clone 3B5) from Oncogene Science/BAYER, 2.5 µg/ml in Ventana antibody dilution buffer).

An intensification kit is used to subsequently obtain a more intensive staining result. This kit consists of a rabbit anti-mouse immunoglobulin, which reacts with the previously bound primary antibody, and of a mouse anti-rabbit immunoglobulin which in turn binds to the previous rabbit anti-mouse immunoglobulin. The incubation time is in each case 8 min. The next reagent to be employed, which is likewise incubated for 8 min, is a "MultiLink" antibody which is directed against both mouse and rabbit and which is coupled to biotin. This antibody now binds to all three previously incubated antibodies and greatly increases the quantity of biotin at the reaction site of the primary antibody. The next reagent to be employed is streptavidin-HRP (Horse Radish Peroxidase), which is added for 8 min and which binds to the biotin. The detection is effected by adding DAB (diaminobenzidine) and $H_2O_2$ as substrate for the peroxidase, with this substrate being converted into a brown precipitate.

The detection of the second marker corresponds precisely to the above-described procedure, beginning with the blocking with 1.5% goat serum and incubation of the second specific primary antibody (p53, clone D01 from Oncogene Science/BAYER, 30 µg/ml in Ventana antibody dilution buffer) for 30 min. At the conclusion, a streptavidin-ALP (alkali phosphatase) conjugate is used in place of the streptavidin-HRP conjugate. After this incubation, the endogenous alkaline phosphatase is blocked with levamisole $+MgCl_2$. The ALP substrate (Fast Red and naphthol) are also added at the same time. Subsequently, the nuclei are counterstained with haematoxylin for 2 min and, after that, the sections are stained for 2 min in "bluing reagent". Finally, the microscope slides are covered with Moviol™ (Hoechst).

Description of an Experiment for Automatically Detecting Abnormal Cells in a Tissue Sample which Cells have Been Stained By Simultaneously Detecting Two Molecular Markers Biopsies in which at least two molecular markers have been detected with antibodies in accordance with the above-described methods are analysed using a fluorescence microscope fitted with an actuatable cross-stage for up to 8 microscope slides (Olympus AX70 having a 2000-3 multicontrol box and "Modul Stage™" analySIS drive software), and a modified version of the Soft Imaging Systems GmbH (SIS) analySIS 3.0 software, which, as an SIS "Grabbit Dual Pro" package, contains additional modules, in particular an FFT (="Fast Fourier Transformation") module, an MIA (="Multiple Image Alignment") module and a C module. High resolution black and white (MV2 Slow Scan Camera, 12 Bit, from SIS) and colour (DXC-950P 3CCD Chip, from Sony) cameras were used for taking the images. In combination, these systems are suitable for a 16 bit Grauton image analysis and for colour image analysis in the RGB and HIS colour spacer up to 24-bit image depth.

After calibrating the actuatable cross-stage (analySIS module stage), the positions, relative to the logical zero point, of in all up to eight microscope slides are recorded by defining eight consecutive stage paths in the "automation" menu (analySIS module grains). The total area of the biological samples is comprehensively subdivided into individual regions having a size of 158.7 µm×119.6 µm, which corresponds to the image sector of a photograph at 40-fold magnification using the microscopic unit. Each biological sample is analysed through a stage path. Each stage path is described horizontally, in a meandering manner, as a series of stage path positions such that each region of the biological sample of the respective microscope slide position is recorded by one stage path position in an abutting manner and not overlapping. Corresponding line numbers and column numbers are defined. The addition of the eight stage paths in the "automation" menu enables all the preparations positioned on the working stage to be analysed in an automated manner.

The preparation stainings at each stage path position are photographed in transmitted light and the image information is "matched to RGB" in the "oper" menu under "colour matching". This enables the subsequent "measurement" to be performed in the "automation" menu. For the measurement, threshold values for up to eight different colour mixtures are defined in the "images" menu by means of "setting colour threshold values" and determining pixel values using "pixel values/new". By means of "phase analysis" in the "measurement" menu, the individual photographs of the respective stage path positions are measured with the aid of the colour threshold values which have been defined and regions of particular colour mixtures are displayed quantitatively, as areas, in an Excel data file. When simultaneously detecting two markers, the colours of the detection reactions, i.e. "brown" (DAB) and "red" (FastRed), and also their intermixture ("red-brown") in a sample region are of particular interest. Consequently, an Excel table is obtained for each individual stage path (=sample), with each column representing the areas for a particular colour mixture. The lines of the Excel table correspond to the individual photographs (=stage path positions) of a single sample region.

Using a macro, the individual values (=measured area of a colour mixture) in a line (=stage part position) are in each case compared with a defined threshold value which is predetermined for the respective column or colour mixture. The macro then accredits the individual values such that the sample is characterized as being diseased if more than one individual value in a line is greater than the colour mixture threshold value which is defined for the respective column.

The corresponding image positions can be stored so that they are available for a subsequent visual appraisal. The "protocol" recording card in the "automation" menu can be used to automatically store images and other data for the respective stage path positions.

While these steps can be performed manually, they can also be carried out in an automated manner by macros being generated in the "extras" menu under "record macros" and subsequently being retrieved in the "automation" menu. Ultimately, a quantitative assessment in the form of an area value (=area on the biological sample which exhibits precisely defined secondary colours as a result of the staining with molecular markers) is obtained for particular colour mixtures. In this way, a diagnostic conclusion for the biological sample is arrived at by quantitatively analysing the accredited colour mixtures.

The invention claimed is:

1. An automatable method for identifying cancer cells and their precursor cells in a cell sample or tissue sample, said method comprising the following steps:
   a) selecting at least two molecular markers of cancer, wherein the detection of each of said markers alone is not a reliable indicator of the presence of cancer cells and their precursor cells in said cell sample or tissue sample,
   b) contacting the cell sample or tissue sample with signaling reagents that specifically bind to said at least two molecular markers,
   c) simultaneously detecting signal intensities from the markers within a single cell of said cell sample or within a constituent region of a section of said tissue sample,
   d) combining and accrediting the signal intensities detected, and comparing the combined and accredited signal intensities to a threshold value, wherein combined and accredited signal intensities above or below the threshold value indicate the presence of cancer cells and their precursors in said cell sample or tissue sample, wherein steps b)-d) collectively comprise:
   i) staining each marker an individual color that is different from a color that every other marker is stained;
   ii) defining a threshold value for a plurality of secondary colors of mixtures of said individual colors;
   iii) determining the presence of multiple markers with a single cell of said cell sample or within a constituent region of a section of said tissue sample by detecting the secondary color of a mixture of said individual colors within said cell or within said constituent region of said tissue sample section; and
   iv) relating the secondary color detected to the threshold value, wherein a value of the secondary color detected above or below the threshold value is predetermined to be indicative of the presence of cancer cells and their precursors in the cell sample or tissue sample.

2. The method according to claim 1, further comprising the step of automatically processing the signal intensities into image information and consolidating said information into a proposed diagnosis using a linked diagnostic expert system.

3. The method according to claim 1, wherein the signaling reagents produce chromogenic color or fluorescence.

4. The method according to claim 1, wherein the at least two molecular markers are selected from the group consisting of:
   her2/neu and Ki67, her2/neu and p53, her2/neu and bcl-2, Her2/neu and MN, her2/neu and mdm-2, her2/neu and EGF receptor, bcl-2 and Ki67, bcl-2 and MN, bcl-2 and mdm-2, bcl-2 and EGF receptor, her2/neu and bcl-2, p53 and bcl-2, p53 and MN, p53 and mdm-2, p53 and EGF receptor, p16 and p53, p16 and MN, p16 and mdm-2, p16 and EGF receptor, p16 and Ki67, p16 and her2/neu, p16 and bcl-2, MN and mdm-2, MN and EGF receptor, mdm-2 and EGF receptor.

5. The method according to claim 1, wherein the sample is obtained from tumors of the mammary gland, the lung, the cervix, the colon, the skin and the prostate.

6. The method according to claim 1, wherein the at least two molecular markers are selected from the group consisting of her2/neu, p16, p53, Ki67, MN, mdm-2, bcl-2, and EGF receptor.

7. The method according to claim 1, wherein step c) comprises simultaneously detecting signal intensities from the markers within a cell.

8. The method according to claim 1, wherein step c) comprises simultaneously detecting signal intensities from the markers within a constituent region of a section of said tissue sample.

* * * * *